(12) United States Patent
Wu et al.

(10) Patent No.: US 9,381,963 B2
(45) Date of Patent: Jul. 5, 2016

(54) VEHICLE PULLING DEVICE, SYSTEM FOR PASSING VEHICLE IN TWO MODES, AND INSPECTION SYSTEM THEREOF

(71) Applicant: NUCTECH COMPANY LIMITED, Beijing (CN)

(72) Inventors: Yucheng Wu, Beijing (CN); Yuan He, Beijing (CN); Zhansen Ran, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 94 days.

(21) Appl. No.: 14/337,176

(22) Filed: Jul. 21, 2014

(65) Prior Publication Data
US 2015/0030124 A1 Jan. 29, 2015

(30) Foreign Application Priority Data
Jul. 23, 2013 (CN) .......................... 2013 1 0310974

(51) Int. Cl.
*B62D 65/18* (2006.01)
*B65G 35/06* (2006.01)
(Continued)

(52) U.S. Cl.
CPC ................. *B62D 65/18* (2013.01); *B60S 13/00* (2013.01); *B65G 35/06* (2013.01); *G01N 23/04* (2013.01); *G01V 5/0016* (2013.01)

(58) Field of Classification Search
CPC . G01V 5/0008; G01V 5/0016; G01V 5/0025; G01V 5/0033; G01V 5/0041; G01V 5/005; G01V 5/0058; G01V 5/0066; B60S 13/00; B60S 13/02; B62D 65/18; B62D 35/06; G01N 23/04
USPC .................................................... 378/57, 208
See application file for complete search history.

(56) References Cited

U.S. PATENT DOCUMENTS

| 5,651,319 A | 7/1997 | Sugahara |
| 6,192,104 B1 * | 2/2001 | Adams ................. G01N 23/203 378/149 |

(Continued)

FOREIGN PATENT DOCUMENTS

| CN | 2752211 Y | 1/2006 |
| CN | 200974538 Y | 11/2007 |

(Continued)

OTHER PUBLICATIONS

European Patent Application No. 14175417.6; Extended Search Report; dated Sep. 4, 2015; 5 pages.

(Continued)

*Primary Examiner* — Allen C. Ho
(74) *Attorney, Agent, or Firm* — Baker & Hostetler LLP (57) ABSTRACT

A vehicle pulling device, a system for passing a vehicle in two modes, and an inspection system for scanning a vehicle by radiation are disclosed. The vehicle pulling device comprises a movable chassis disposed in a passage for a vehicle and being movable in a first direction; and a support beam disposed to the movable chassis and being rotatable between a first position and a second position. In the first position, the support beam is located substantially in a second direction substantially perpendicular to the first direction, such that wheels of the vehicle are interacted with the support beam of the vehicle pulling device so that the vehicle is pulled to pass through the passage; and in the second position, the support beam is located substantially parallel to the first direction such that the wheels of the vehicle are not interacted with the support beam of the vehicle pulling device so that the vehicle travels by itself to pass through the passage. Therefore, when the vehicle does not need to be pulled, the support beam is rotated to the second position, and the vehicle travels by itself to pass through the passage. When the support beam is rotated to the first position, the vehicle pulling device can pull the vehicle to pass through the passage.

15 Claims, 9 Drawing Sheets

(51) Int. Cl.
 *B60S 13/00* (2006.01)
 *G01V 5/00* (2006.01)
 *G01N 23/04* (2006.01)

(56) References Cited

U.S. PATENT DOCUMENTS

| | | | | |
|---|---|---|---|---|
| 6,542,580 B1 * | 4/2003 | Carver | G01V 5/0008 | 378/57 |
| 6,763,635 B1 * | 7/2004 | Lowman | B60P 1/5433 | 378/198 |
| 6,920,197 B2 * | 7/2005 | Kang | G01V 5/0008 | 378/198 |
| 6,928,141 B2 * | 8/2005 | Carver | G01N 23/04 | 378/197 |
| 7,103,137 B2 * | 9/2006 | Seppi | G01N 23/04 | 378/57 |
| 7,350,613 B2 * | 4/2008 | Dehne | B62D 65/18 | 180/167 |
| 7,356,116 B2 * | 4/2008 | Anwar | G01V 5/0016 | 378/57 |
| 7,369,643 B2 * | 5/2008 | Kotowski | G01N 23/04 | 378/197 |
| 7,379,530 B2 * | 5/2008 | Hoff | G01V 5/0016 | 378/108 |
| 7,400,701 B1 * | 7/2008 | Cason | G01V 5/0025 | 378/57 |
| 7,497,618 B2 * | 3/2009 | Chen | G01V 5/0016 | 378/198 |
| 7,526,064 B2 * | 4/2009 | Akery | G01N 23/04 | 378/198 |
| 7,660,386 B2 * | 2/2010 | Meng | G01V 5/0008 | 378/189 |
| 7,663,109 B2 * | 2/2010 | Kang | G01V 5/0016 | 350/359.1 |
| 7,702,070 B2 * | 4/2010 | Kang | G01V 5/005 | 378/195 |
| 7,706,502 B2 * | 4/2010 | Bueno | G01V 5/0016 | 378/19 |
| 7,722,251 B2 * | 5/2010 | Kang | G01V 5/0008 | 378/10 |
| 7,742,568 B2 * | 6/2010 | Smith | G01N 23/087 | 378/57 |
| 7,780,390 B2 * | 8/2010 | Fujiwara | G01V 5/0008 | 378/198 |
| 7,783,004 B2 * | 8/2010 | Kotowski | G01N 23/04 | 378/57 |
| 7,819,580 B2 * | 10/2010 | Song | G01V 5/0016 | 378/147 |
| 7,845,286 B2 * | 12/2010 | Hu | G01V 5/0008 | 104/162 |
| 7,848,485 B2 * | 12/2010 | Hu | G01V 5/0008 | 378/208 |
| 7,929,664 B2 * | 4/2011 | Goodenough | G01V 5/005 | 378/53 |
| 8,155,384 B2 * | 4/2012 | Chew | G01V 5/0008 | 348/143 |
| 8,230,988 B2 * | 7/2012 | Tada | B62D 65/18 | 198/346.2 |
| 8,295,433 B2 * | 10/2012 | Linev | G01V 5/0033 | 37/205 |
| 8,340,245 B2 * | 12/2012 | Herranz | G01N 23/04 | 378/4 |
| 8,345,819 B2 * | 1/2013 | Mastronardi | G01V 5/0008 | 378/198 |
| 8,382,408 B2 * | 2/2013 | Sun | B61J 3/00 | 410/67 |
| 8,472,583 B2 * | 6/2013 | Star-Lack | G01V 5/005 | 378/4 |
| 8,582,720 B2 * | 11/2013 | Morton | B01V 5/0008 | 378/57 |
| 8,615,067 B2 * | 12/2013 | Hayes | G01V 5/0008 | 378/51 |
| 8,824,632 B2 * | 9/2014 | Mastronardi | G01V 5/0033 | 378/57 |
| 8,903,046 B2 * | 12/2014 | Morton | G01V 5/0025 | 378/87 |
| 8,971,487 B2 * | 3/2015 | Mastronardi | G01V 5/0008 | 378/57 |
| 9,036,779 B2 * | 5/2015 | Morton | G01V 5/0041 | 378/150 |
| 9,057,679 B2 * | 6/2015 | Morton | G01N 23/04 | |
| 2008/0159840 A1 | 7/2008 | Hu et al. | | |
| 2009/0067962 A1 | 3/2009 | Lee | | |

FOREIGN PATENT DOCUMENTS

| | | |
|---|---|---|
| CN | 102107767 A | 6/2011 |
| CN | 203382122 U | 1/2014 |
| DE | 4446835 A1 | 7/1996 |
| EP | 1486390 A2 | 12/2004 |
| WO | WO 99/46188 A1 | 9/1999 |
| WO | WO 2004/035967 A1 | 4/2004 |

OTHER PUBLICATIONS

Great Britain Patent Application No. 1412365.7; Combined Search Report and Exam Report; dated Jan. 15, 2015; 6 pages.

* cited by examiner

VEHICLE PULLING DEVICE, SYSTEM FOR PASSING VEHICLE IN TWO MODES, AND INSPECTION SYSTEM THEREOF

CROSS-REFERENCE TO RELATED APPLICATIONS

This application claims priority to Chinese Patent Application No. 201310310974.5 filed Jul. 23, 2013, the disclosures of which are incorporated herein by reference in their entireties.

BACKGROUND OF THE INVENTION

1. Field of the Invention

The present invention relates to a vehicle pulling device, a system for passing a vehicle in two modes, and an inspection system for scanning a vehicle by radiation.

2. Description of the Related Art

During safety inspection of a vehicle, the vehicle needs to travel along a passage while for example, an X-ray emission device on one side of the passage is used to emit X-rays and the X-rays are received by an X-ray receiving device on the other side of the passage after passing through the vehicle, thereby determining whether there is a contraband item in the vehicle.

SUMMARY OF THE INVENTION

An object of the present invention is to provide a vehicle pulling device, a system for passing a vehicle in two modes, and an inspection system for scanning a vehicle by radiation, thereby achieving two inspection modes in which one is a vehicle travels by itself to pass through a passage and the other is the vehicle is pulled to pass through the passage.

In accordance with an aspect of the present invention, there is provided a vehicle pulling device comprising: a movable chassis disposed in a passage for a vehicle and being movable in a first direction; and a support beam disposed to the movable chassis and being rotatable between a first position and a second position, wherein in the first position, the support beam is located substantially in a second direction substantially perpendicular to the first direction, such that wheels of the vehicle are interacted with the support beam of the vehicle pulling device so that the vehicle is pulled to pass through the passage; and in the second position, the support beam is located substantially parallel to the first direction such that the wheels of the vehicle are not interacted with the support beam of the vehicle pulling device so that the vehicle travels by itself to pass through the passage.

In accordance with an aspect of the present invention, there is provided a vehicle pulling device comprising: a movable chassis movable in a first direction; and a support beam disposed to the movable chassis to be rotatable in a substantially horizontal plane and to be rotatable to a first position and a second position, wherein in the first position, the support beam is located substantially in a second direction substantially perpendicular to the first direction; and in the second position, a size of the support beam in the second direction is less than a predetermined value.

In accordance with an aspect of the present invention, the vehicle pulling device further comprises a driven member disposed to the movable chassis and connected to the support beam, wherein the driven member is configured to be driven by a driving member that is disposed in a passage where the movable chassis travels, by movement of the movable chassis in the first direction, thereby rotating the support beam to the first or the second position.

In accordance with an aspect of the present invention, when the movable chassis is located in a first travel position, the driven member begins to be driven by the driving member, and when the movable chassis travels to a second travel position, the driven member is separated from the driving member.

In accordance with an aspect of the present invention, the driven member is a friction wheel, while the driving member is a friction belt.

In accordance with an aspect of the present invention, the friction wheel is connected to the support beam through a shaft.

In accordance with an aspect of the present invention, the driven member is disposed below the movable chassis.

In accordance with an aspect of the present invention, the vehicle pulling device further comprises a position limit member for limiting a rotation range of the friction wheel, wherein the friction wheel has a recess extending in a circumferential direction and having a first end and a second end, and the position limit member is capable of contacting with the first end and the second end to limit the rotation range of the friction wheel.

In accordance with an aspect of the present invention, the support beam has depressed portions on an upper surface of both ends, wherein when the support beam is in the first position, the wheels of the vehicle are engaged with the depressed portions on the upper surface of both ends of the support beam so that the vehicle is pulled to pass through the passage.

In accordance with an aspect of the present invention, each of the two ends of the support beam has ramp portions on both sides, and the depressed portion is located between the ramp portions.

In accordance with an aspect of the present invention, the vehicle pulling device further comprises a position limit member for limiting a rotation range of the friction wheel, wherein the position limit member limits the rotation range of the friction wheel within a range of about 90 degrees.

In accordance with another aspect of the present invention, there is provided a system for passing a vehicle in two modes comprising a passage through which a vehicle passes; and a vehicle pulling device disposed in the passage, the vehicle pulling device comprising: a movable chassis movable in a first direction in which the vehicle travels; and a support beam disposed to the movable chassis and being rotatable between a first position and a second position, wherein in the first position, the support beam is located substantially in a second direction substantially perpendicular to the first direction, such that wheels of the vehicle are interacted with the support beam of the vehicle pulling device so that the vehicle is pulled to pass through the passage; and in the second position, the support beam is located substantially parallel to the first direction such that the wheels of the vehicle are not interacted with the support beam of the vehicle pulling device so that the vehicle travels by itself to pass through the passage.

In accordance with a further aspect of the present invention, the system further comprises a groove disposed in a ground surface in the passage, wherein the movable chassis travels in the groove.

In accordance with a further aspect of the present invention, when the support beam is in the second position, bottom surfaces of the two ends of the support beam are higher than the ground surface.

In accordance with a further aspect of the present invention, the groove is located substantially at a middle portion of the passage in the second direction.

In accordance with a still further aspect of the present invention, there is provided an inspection system for scanning a vehicle by radiation comprising: a passage through which a vehicle passes, a radiation source disposed on one side of the passage, a radiation receiving device disposed on the other side of the passage to receive the radiation passing through the vehicle under inspection, and a vehicle pulling device for enabling the vehicle to pass through the passage in a first direction in a first mode and a second mode, wherein in the first mode, a support beam of the vehicle pulling device is located substantially in a second direction substantially perpendicular to the first direction, such that wheels of the vehicle are interacted with the support beam of the vehicle pulling device so that the vehicle is pulled to pass through the passage; and in the second mode, the support beam is located substantially parallel to the first direction such that the wheels of the vehicle are not interacted with the support beam of the vehicle pulling device so that the vehicle travels by itself to pass through the passage.

The present invention can achieve two inspection modes in which one is a vehicle travels through the passage by itself and the other is the vehicle is pulled to pass through the passage, by means of rotation of the support beam to the first position and the second position.

DETAILED DESCRIPTION OF THE EMBODIMENTS

A further description of the invention will be made as below with reference to embodiments of the present invention taken in conjunction with the accompanying drawings.

As shown in FIGS. 1-9, an inspection system 10 for scanning a vehicle 20 by radiation according to an embodiment of the present invention comprises: a passage 15 (FIGS. 8A and 8B) through which a vehicle 20 passes, an X-ray source 13 (FIGS. 6A and 7A) disposed on one side of the passage 15 to emit an X-ray beam, an X-ray receiving device 14 (FIGS. 6A and 7A) disposed on the other side of the passage 15 to receive the X-ray beam passing through the vehicle 20 under inspection, and a vehicle pulling device 100 for pulling the vehicle 20 to pass through the passage 15 (for example, a radiation scanning inspection region). A groove 12 (FIG. 1) may be disposed in a ground surface within the passage 15.

Figure 4:
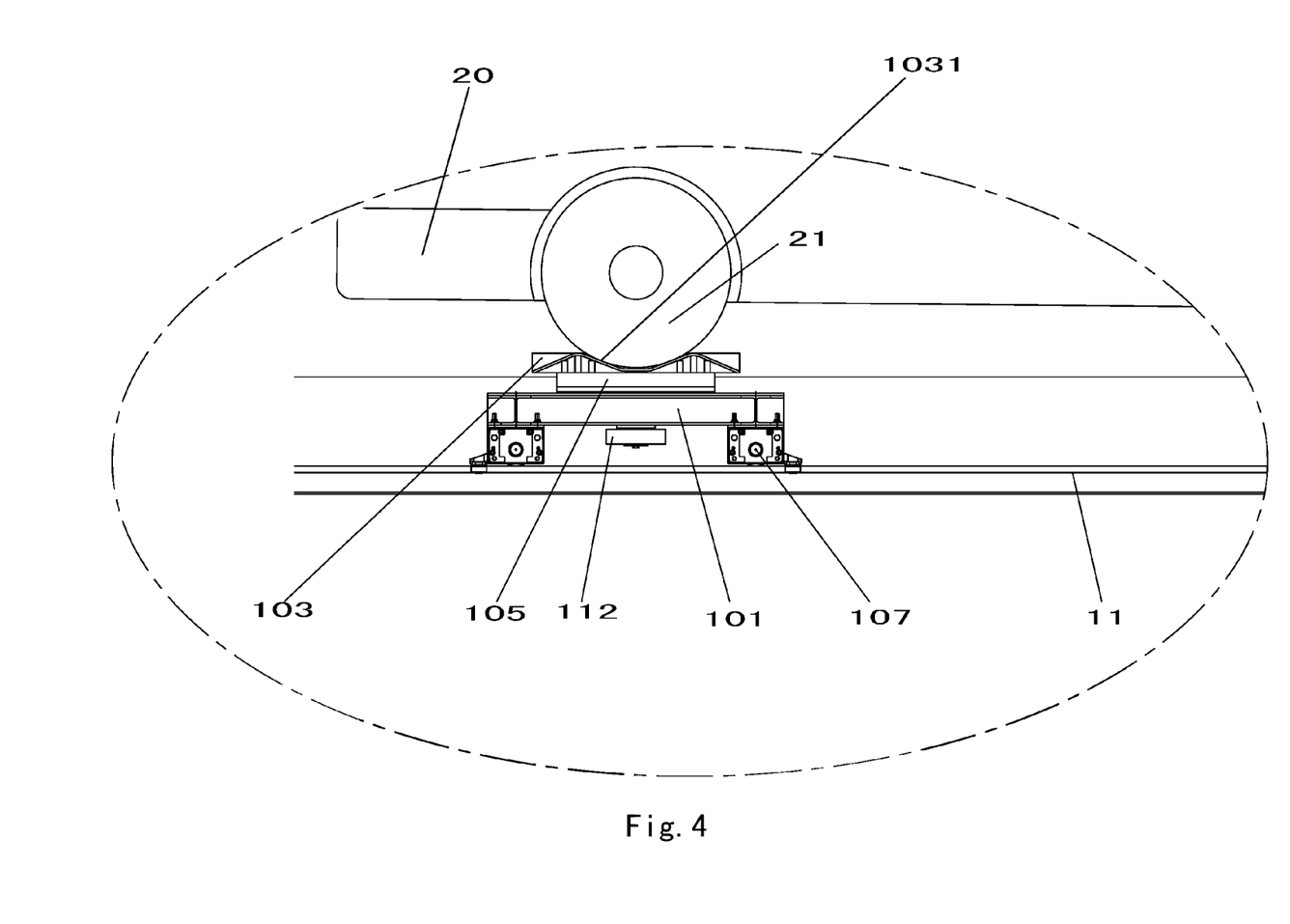
FIG. 4 is a partially enlarged schematic view showing a draft vehicle according to an embodiment of the present invention in which front wheels of a vehicle have been lifted by the draft vehicle.
Figure 5:
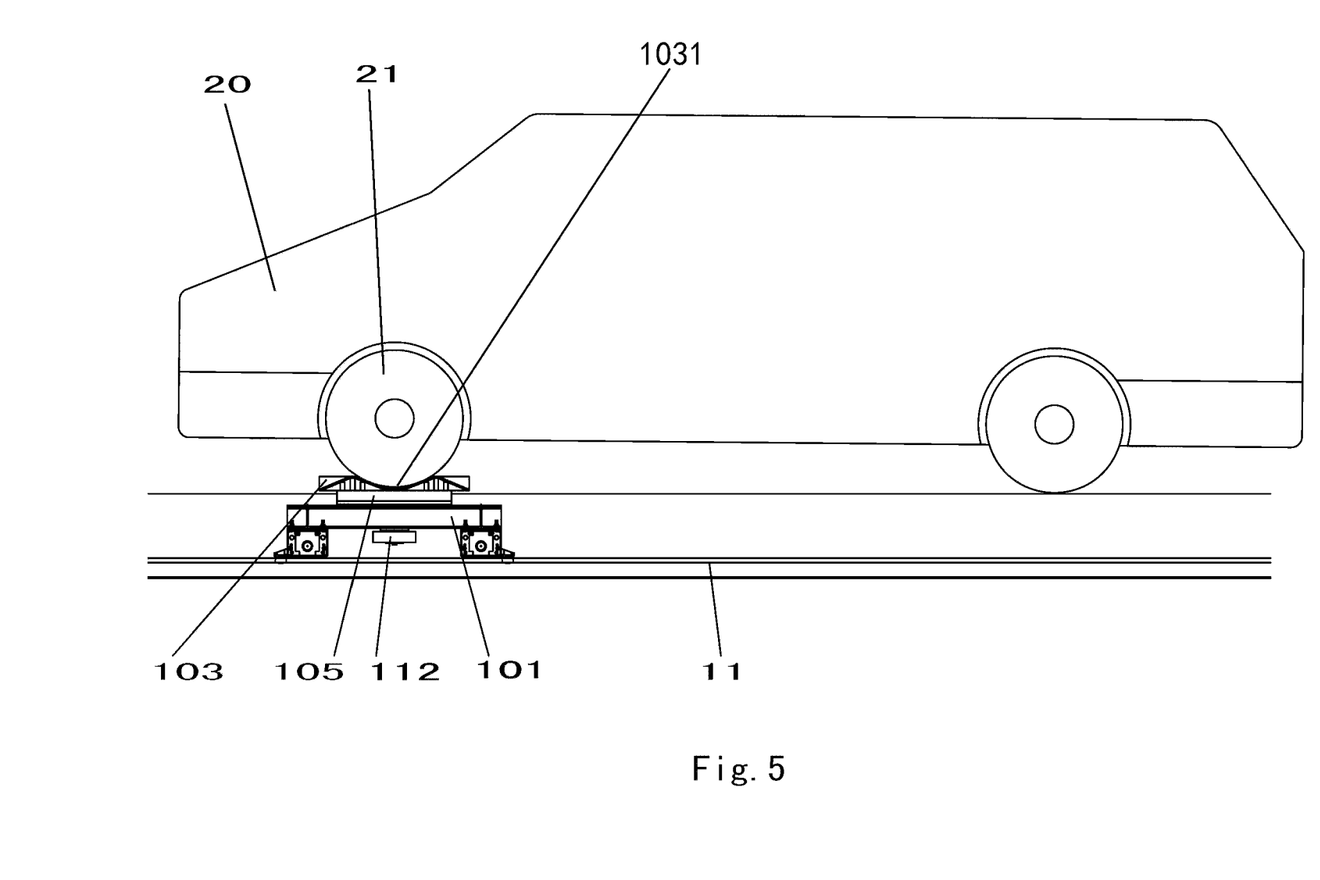
FIG. 5 is a schematic side view showing the vehicle pulling device according to the embodiment of the present invention in which the vehicle is pulled by the vehicle pulling device.
Figure 6A:
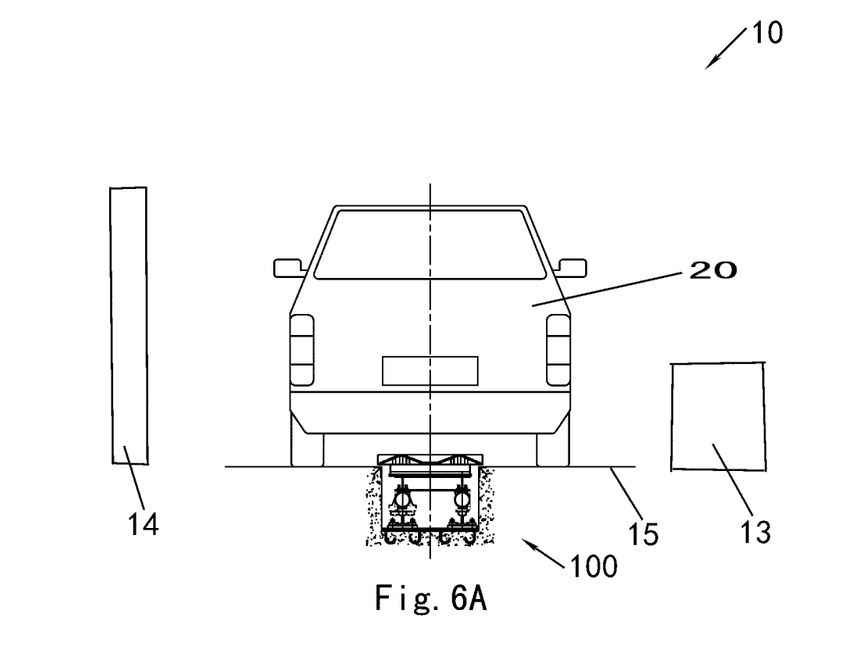
FIGS. 6A and 6B are schematic views showing a state where the vehicle passes through a passage by itself.
Figure 6B:
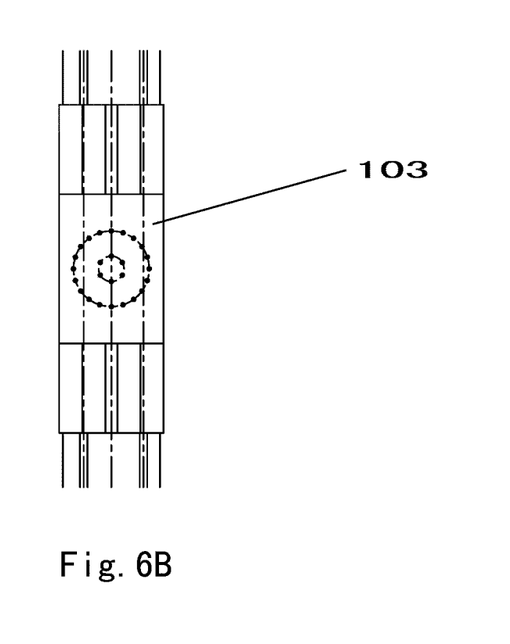
Figure 7A:
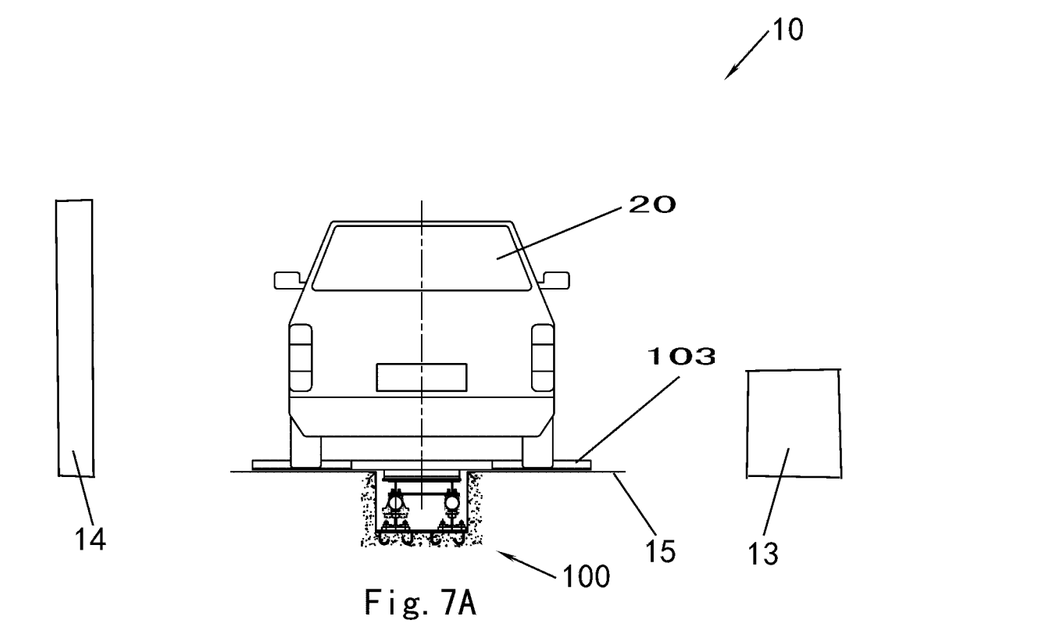
FIGS. 7A and 7B are schematic views showing a state where the vehicle is pulled to pass through the passage.
Figure 7B:
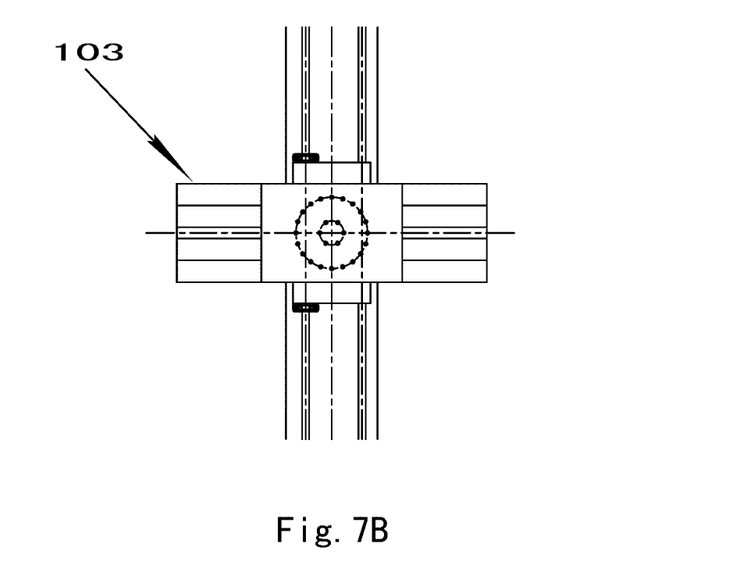
Figures 8A, 8B:
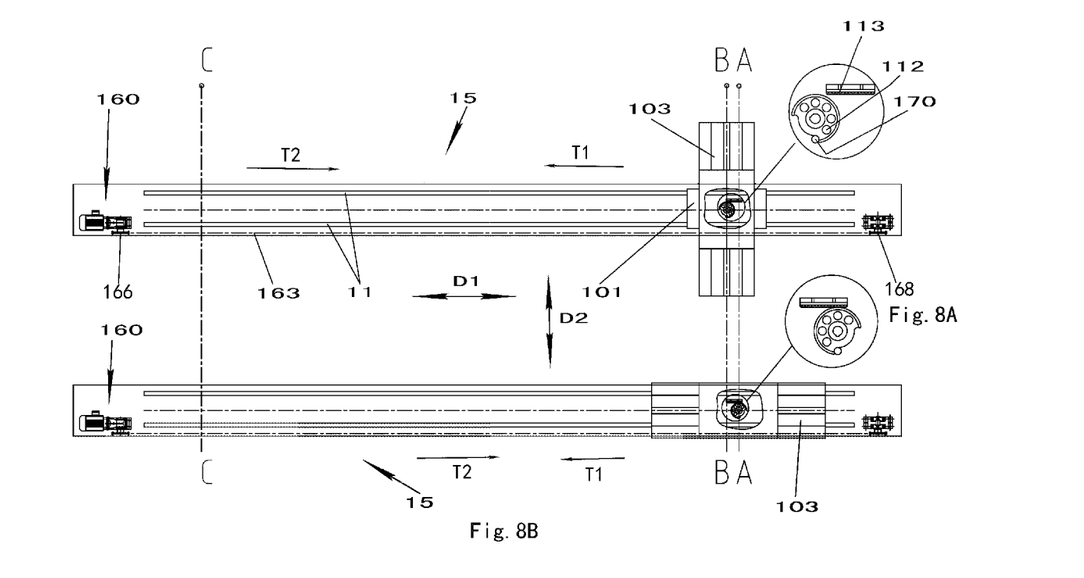
FIGS. 8A and 8B are schematic views showing an operational process of the inspection system for scanning a vehicle by radiation according to the embodiment of the present invention.

As shown in FIGS. 1-9, the vehicle pulling device 100 comprises: a movable chassis 101 movable in a first direction D1 (such as a longitudinal direction of the passage), and a support beam 103 disposed to the movable chassis 101 to be rotatable in a substantially horizontal plane and to be rotatable to a first position (a position shown in FIGS. 7A, 7B and 8A) and a second position (a position shown in FIGS. 6A, 6B and 8B). In the first position, the support beam 103 (for example, the longitudinal direction of the support beam 103) is located substantially in a second direction D2 (i.e., a transverse direction of the passage) substantially perpendicular to the first direction, and in the second position, a size of the support beam 103 in the second direction D2 is less than a predetermined value. In other words, the support beam 103 is rotatable between the first position (the position shown in FIGS. 7A, 7B and 8A) and the second position (the position shown in FIGS. 6A, 6B and 8B).

As shown in FIGS. 1-9, the predetermined value may be a distance between left and right wheels of the vehicle 20. As a result, when the support beam 103 is in the second position, the vehicle 20 is allowed to cross the support beam 103 in a state where the support beam 103 is located between the left and right wheels. In other words, in this case, the support beam 103 does not obstruct a drive from driving the vehicle 20 by itself to pass through the passage.

As shown in FIGS. 6A, 6B and 8B, in the second position, the support beam 103 may be substantially parallel to the first direction D1. Alternatively, the support beam 103 may rotate by an angle (an angle less than 90 degrees) relative to the first position so that the vehicle 20 is allowed to cross the support beam 103 in a state where the support beam 103 is located between the left and right wheels and the support beam 103 does not obstruct a drive from driving the vehicle 20 by itself to pass through the passage.

As shown in FIGS. 4, 5, 7A, and 7B, the support beam 103 may have depressed portions 1031 on upper surfaces of both ends. Front wheels 21 of the vehicle 20 may be placed in the depressed portions 1013 so that the vehicle 20 is pulled by the vehicle pulling device 100.

When the vehicle 20 under inspection needs to be pulled to pass through the passage 15, the support beam 103 is rotated to the first position, the front wheels 21 of the vehicle 20 travel into the depressed portions 1031 of the support beam 103, and the movable chassis 101 drives the support beam 103 and the vehicle 20 to pass through the passage 15 together, as shown in FIGS. 7A, 7B, and 8A. When a drive drives the vehicle 20 by itself to pass through the passage 15, the support beam 103 is rotated to the second position, and thereby the support beam 103 does not obstruct the drive from driving the vehicle 20 by itself to pass through the passage 15, as shown in FIGS. 6A, 6B, and 8B.

Figure 1:
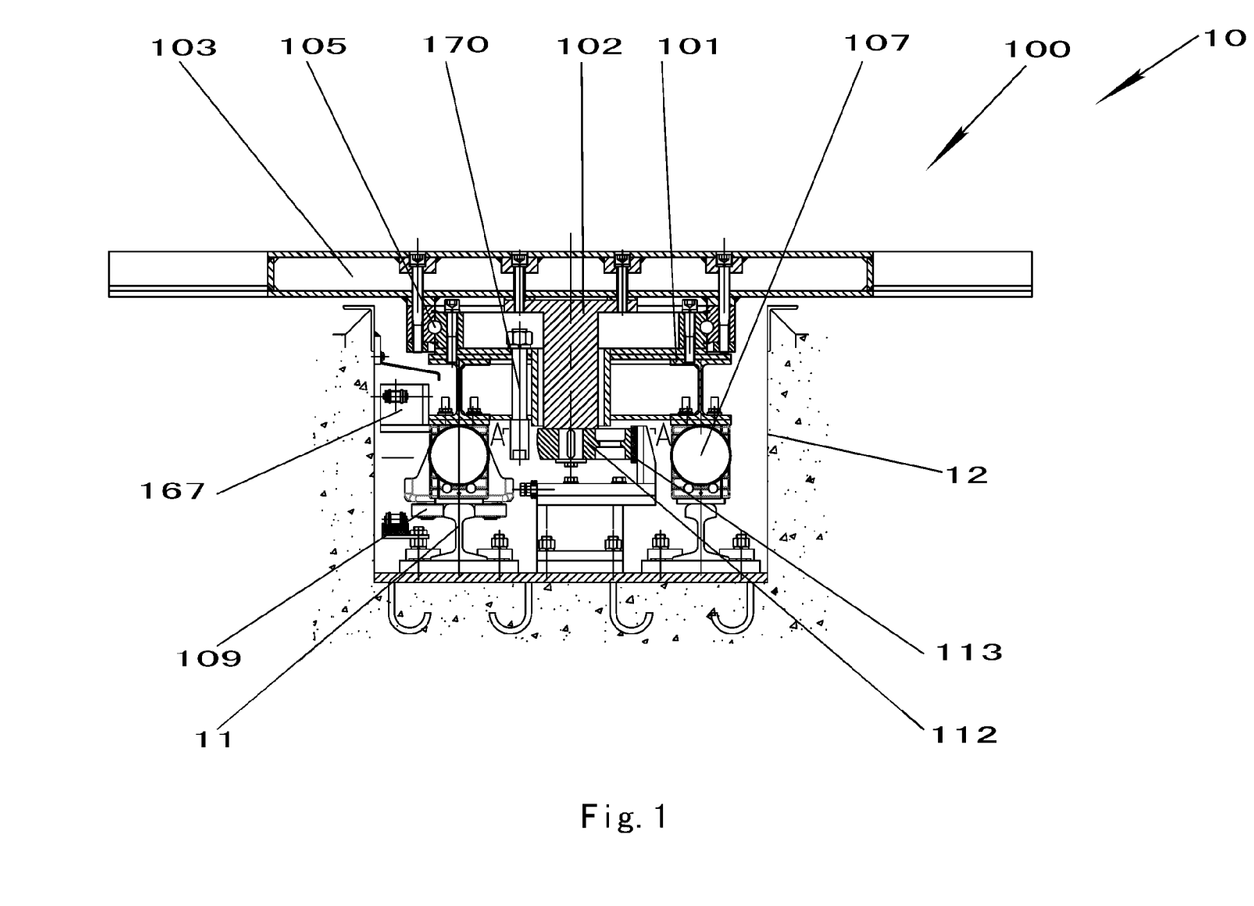
FIG. 1 is a schematic view showing a structure of an inspection system for scanning a vehicle by radiation according to an embodiment of the present invention.

The support beam 103 may be mounted to the movable chassis 101 in any appropriate manner. For example, as shown in FIG. 1, the vehicle pulling device 100 may further comprise a rotary support 105. The support beam 103 is rotatably supported on the movable chassis 101 through the rotary support 105. In addition, the support beam 103 may be rotatably supported directly on the movable chassis 101. For example, the support beam 103 may be mounted to the movable chassis 101 by a shaft.

Figure 9:
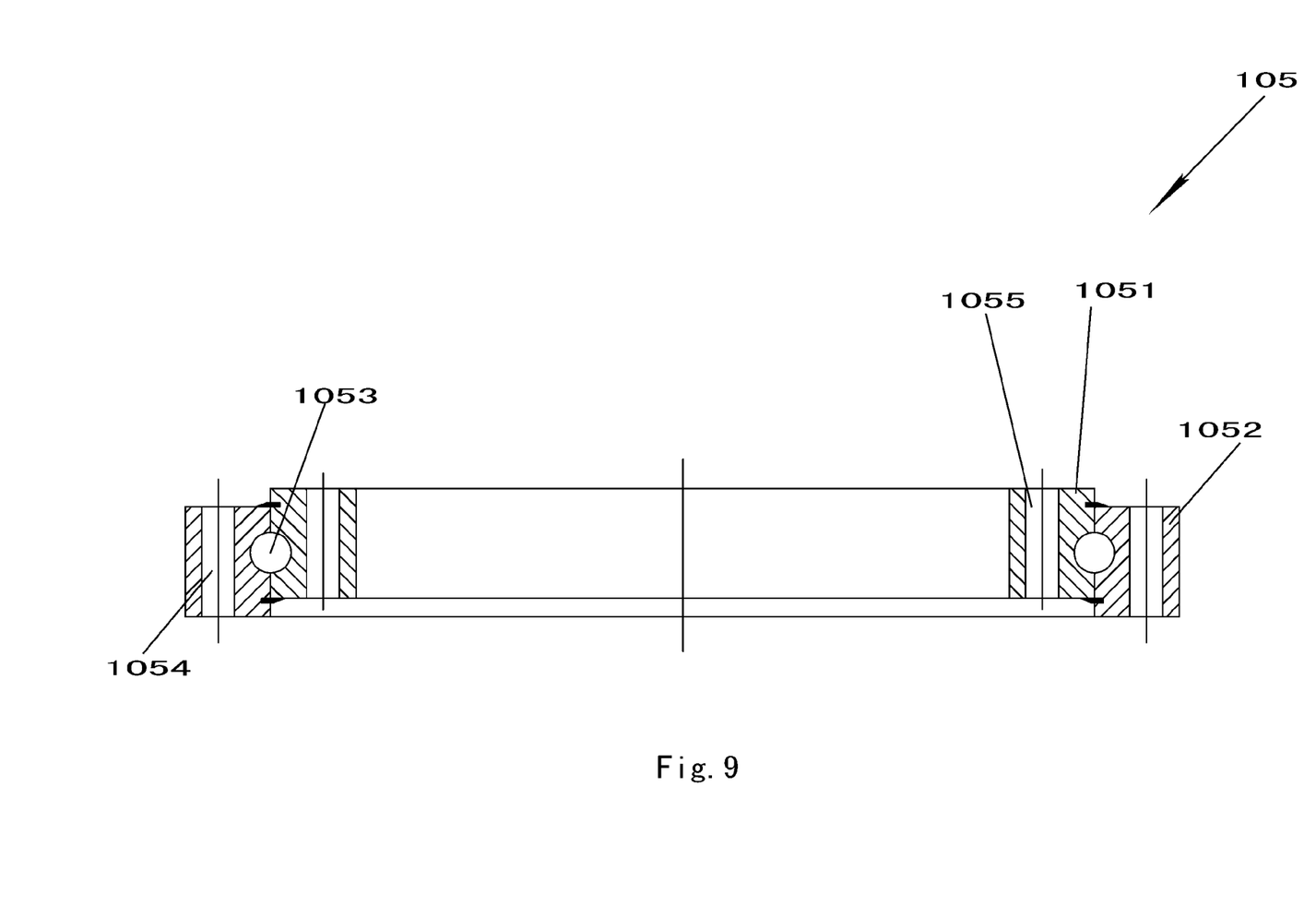
FIG. 9 is a schematic view showing a rotary support of the vehicle pulling device according to the embodiment of the present invention.

As shown in FIG. 9, the rotary support 105 comprises coaxial annular members 1051 and 1052. The annular members 1051 and 1052 are rotatable relative to each other. Balls 1053 are disposed between the annular members 1051 and 1052. The annular members 1051 and 1052 constitute a thrust bearing. The thrust bearing has an inner ring formed by the annular member 1051 and an outer ring formed by the annular member 1052. Furthermore, the annular members 1051 and 1052 are provided with through holes 1055 and 1054, respectively. Bolts pass through the through holes 1055 and 1054 to connect the annular members 1051 and 1052 to the support beam 103 and the movable chassis 101, respectively.

Further, the annular members 1051 and 1052 of the rotary support 105 may be slidably moved relative to each other. In other words, the annular members 1051 and 1052 may constitute a sliding-contact thrust bearing. In addition, the support beam 103 and the movable chassis 101 may be connected together through a standard thrust bearing.

As shown in FIG. 1, the vehicle pulling device 100 may further comprise a wheel set 107 and a guide wheel 109. The movable chassis 101 can travel on a track 11 through the wheel set 107 and the guide wheel 109. In addition, if no wheel set 107 is disposed, the movable chassis 101 can travel on a slide way.

As shown in FIGS. 1, 3, 4, 5, 8A, and 8B, the vehicle pulling device 100 further comprises a driven member 112 disposed to the movable chassis 101 and being connected to the support beam 103. The driven member 112 is configured to be driven by a driving member 113 that is disposed in the passage 15 in which the movable chassis 101 travels, by movement of the movable chassis 101 in the first direction D1, thereby rotating the support beam 103 to the first or the second position. As shown in FIGS. 1, 4, and 5, the driven member 112 is disposed below the movable chassis 101. The driven member 112 may be disposed above the movable chassis 101 without affecting passing of the vehicle 20 through the passage 15.

As shown in FIG. 8B, when the movable chassis 101 is located in a first travel position A, the driven member 112 begins to be driven by the driving member 113, and as shown in FIG. 8A, when the movable chassis 101 travels to a second travel position B, the driven member 112 is separated from the driving member 113.

In an embodiment, the driven member 112 is embodied as a friction wheel, while the driving member 113 is embodied as a friction belt as shown in FIGS. 1-9. Alternatively, for example, the driven member 112 is embodied as a gear, while the driving member 113 is embodied as a rack; or, the driven member 112 is embodied as a linkage mechanism, while the driving member is embodied as a stopper for stopping a link of the linkage mechanism.

Figure 2A:
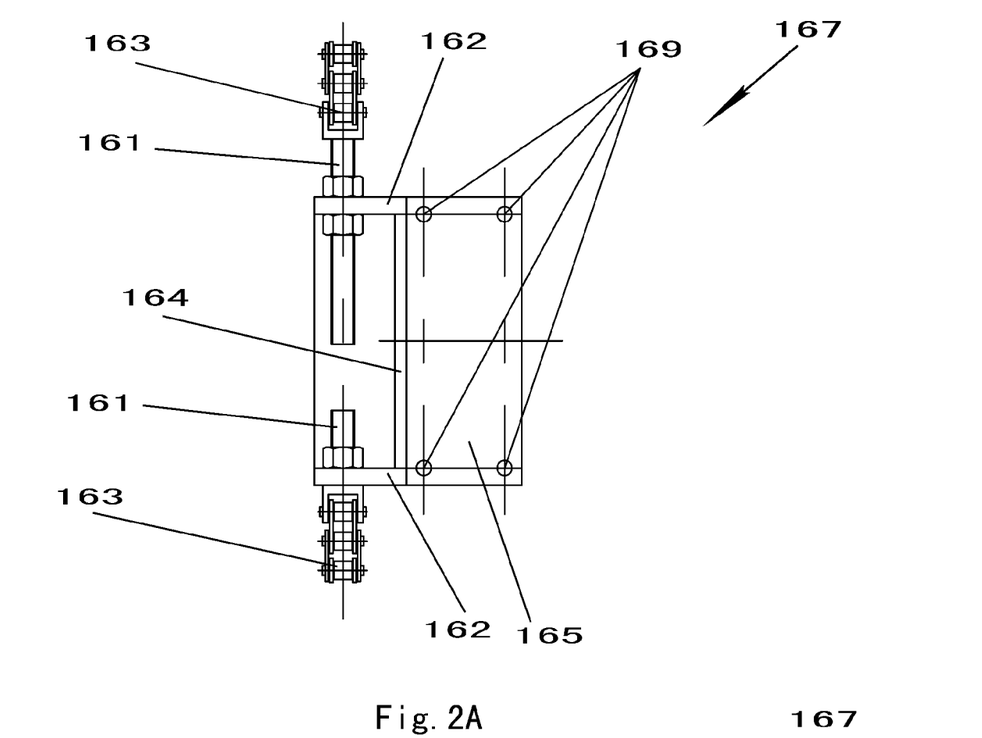
FIGS. 2A and 2B are schematic views showing a structural principle of a chain tensioner of the inspection system for scanning a vehicle by radiation according to the embodiment of the present invention.
Figure 2B:
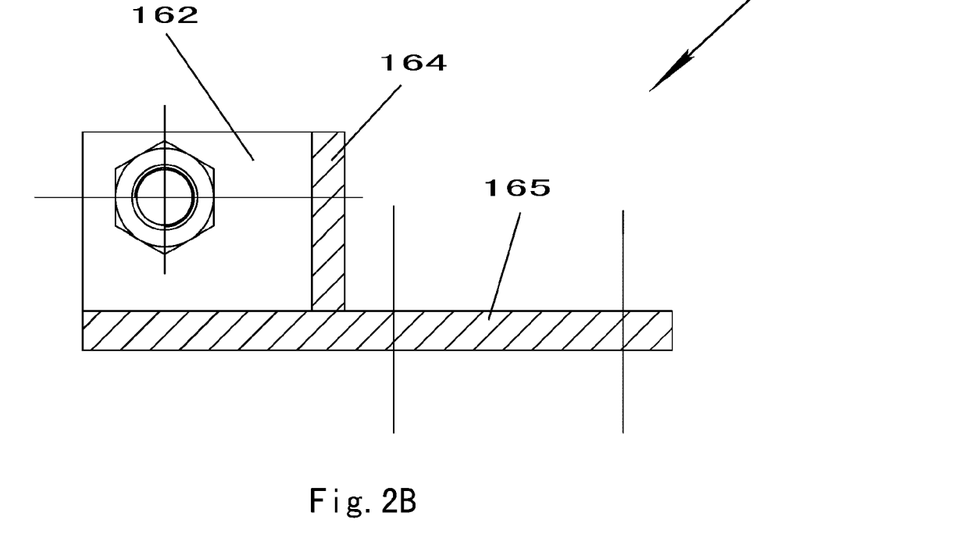
Figure 3:
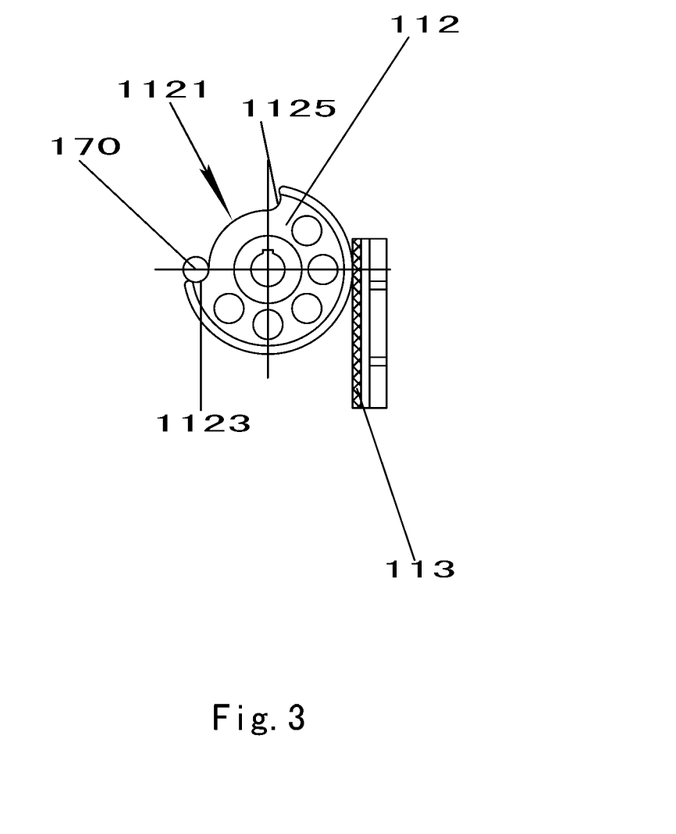
FIG. 3 is a schematic view of a friction mechanism, for driving a rotatable support beam, of a vehicle pulling device according to an embodiment of the present invention.

The movable chassis 101 can travel along the passage 15 in any appropriate manner. For example, the movable chassis 101 itself has a drive device or is driven by other drive device. For example, as shown in FIGS. 8A and 8B, the vehicle pulling device 100 may further comprise a chain type drive device 160. The chain type drive device 160 comprises an electric motor, a speed reducer, a driving chain wheel 166, a chain 163, a driven chain wheel 168. As shown in FIGS. 1, 2A and 2B, the chain 163 is connected to a chain tensioner 167, and the chain tensioner 167 is connected to the movable chassis 101 by passing bolts through these fixing holes 169, thereby driving the movable chassis 101 by the chain 163 to travel.

As shown in FIGS. 2A and 2B, the chain tensioner 167 comprises a fixing plate 165 formed with the fixing holes 169. The chain tensioner 167 further comprises a pair of chain fixing plates 162 and a reinforcing plate 164 which are fixed to a surface of the fixing plate 165. The pair of chain fixing plates 162 are substantially parallel to each other and may be substantially perpendicular to the fixing plate 165. The reinforcing plate 164 is located between the pair of the chain fixing plates 162 and connected to the pair of the chain fixing plates 162. The reinforcing plate 164 may be substantially perpendicular to the pair of chain fixing plates 162. The paired chain fixing plates 162 have coaxial holes. The chain tensioner 167 further comprises a pair of pull rods 161. The pull rods 161 are inserted in the coaxial holes of the pair of the chain fixing plates 162, respectively. Each of the pull rods 161 has one end connected to the chain 163, and the other end provided with a screw thread and fixed to the chain fixing plate 162 by a nut therethrough. The tension of the chain 163 can be adjusted by the nut.

As shown in FIG. 1, the driven member 112 is connected to the support beam 103 through a shaft 102. Alternatively, the driven member 112 may be coupled to the support beam 103 through a speed reduction mechanism. In FIG. 1, the shaft 102 has a flange at its upper end, and the flange is connected to the support beam 103 through screws. Alternatively, the shaft 102 may be connected to the support beam 103 through a spline or in other appropriate manner. The movable chassis 101 has a through hole extending in a vertical direction through which the shaft 102 passes.

As shown in FIGS. 1, 3, 8A, and 8B, the vehicle pulling device 100 may further comprise a position limit member 170 for limiting a rotation range of the driven member 112. The position limit member 170 may be a rod connected to the movable chassis 101. The driven member 112 has a recess 1121 extending in a circumferential direction and having a first end 1123 and a second end 1125, and the position limit member 170 is capable of contacting with the first end 1123 and the second end 1125 to limit the rotation range of the driven member 112. The position limit member 170 may limit the rotation range of the driven member 112 within a range of about 90 degrees. For example, the support beam 103 can rotate in the range of 90 degrees by the friction driving mechanism and the position limit mechanism shown in FIG. 3.

As shown in FIGS. 1, 8A, and 8B, a bottom surface of the support beam 103 is higher than the ground surface of the passage 15 by a predetermined distance such as 10-50 mm, while the other components of the vehicle pulling device 100 may be disposed within the groove 12 in the ground surface of the passage 15. As shown in FIGS. 4 and 5, each of the two ends of the support beam 103 has a ramp portion on either side, and the depressed portion 1031 is located between the ramp portions. As a result, the front wheels 21 of the vehicle 20 can easily roll into the depressed portions 1031 to be positioned in the depressed portions 1031.

An operational manner of the vehicle pulling device 100 according to an embodiment of the present invention is explained as below by taking the driven member 112 and the driving member 113 for example by referring to FIGS. 8A and 8B.

FIG. 8B shows an initial position of the movable chassis 101 in operation, i.e., a mode in which a drive drives the vehicle 20 by itself to pass through the passage 15. The draft vehicle 20 or movable chassis 101 is stopped in the first travel position A. The partially enlarged view shows a relative position between the driven member 112 coaxial with the support beam 103 and the driving member 113 fixed to the ground surface. When the inspection system 10 needs to be switched to a pulling mode as shown in FIG. 8A, the chain 163 of the chain type drive device 160 is driven to move. The chain 163 drives the draft vehicle 20 or movable chassis 101 to move in a first travel direction T1. So long as the draft vehicle 20 or movable chassis 101 travels to the second travel position B (towards the left side in the drawing), the driven member 112 automatically drives the support beam 103 to rotate by 90 degrees under the action of the driving member 113. At this time, the driven member 112 has been separated from the driving member 113 as shown in the partially enlarged view. The second travel position B is a point where the vehicle 20 is loaded (i.e., the vehicle 20 is driven such that the front wheels 21 are moved onto the support beam 103). In the second travel position B, the draft vehicle 20 or movable chassis 101 is stopped, the vehicle 20 is driven such that the front wheels 21 are moved onto the support beam 103. After the front wheels 21 of the vehicle 20 are moved onto the support beam 103, the chain 163 of the chain type drive device 160 is driven to move, and the chain 163 drives the draft vehicle 20 or movable chassis 101 to move in the first travel direction T1. The draft vehicle 20 and the movable chassis 101 drives the vehicle 20 from the second travel position B to a third travel position C (towards the left side in the drawing), thereby completing the inspection. The inspected vehicle 20 is driven to leave the passage 15. If a next vehicle 20 still needs to be pulled for the inspection, the chain 163 of the chain type drive device 160 is driven to move, and the chain 163 drives the draft vehicle 20 or movable chassis 101 to move in a second travel direction T2 opposite to the first travel direction T1. The draft vehicle 20 or movable chassis 101 is returned only to the second travel position B and the loading and inspection are repeated.

If the next vehicle 20 does not need to be pulled for the inspection, the chain 163 of the chain type drive device 160 is driven to move, and the chain 163 drives the draft vehicle 20 or movable chassis 101 to move in the second travel direction T2. The draft vehicle 20 or movable chassis 101 is returned directly to the first travel position A. During the travelling of the draft vehicle 20 or movable chassis 101 from the second travel position B to the first travel position A, the driven member 112 is in contact with the driving member 113, and thus the support beam 103 automatically rotates to the initial state, i.e., the state shown in FIG. 8B.

In an embodiment, the support beam 103 is rotated only manually. Therefore, in this case, it is not necessary to provide the driven member 112 and the driving member 113.

In addition, the vehicle pulling device according to the present invention is also applicable to any appropriate system, and is not limited to the application in an inspection system for scanning a vehicle by radiation. Furthermore, the vehicle pulling device can form a system for passing a vehicle in two modes.

The invention claimed is:

1. A vehicle pulling device comprising:
a movable chassis disposed in a passage for a vehicle and being movable in a first direction; and
a support beam disposed to the movable chassis and being rotatable between a first position and a second position, wherein:
in the first position, the support beam is located substantially in a second direction substantially perpendicular to the first direction, such that wheels of the vehicle are interacted with the support beam of the vehicle pulling device so that the vehicle is pulled to pass through the passage; and in the second position, the support beam is located substantially parallel to the first direction such that the wheels of the vehicle are not interacted with the support beam of the vehicle pulling device so that the vehicle travels by itself to pass through the passage.

2. The vehicle pulling device of claim 1, further comprising:
a driving member disposed in the passage where the movable chassis travels; and
a driven member disposed to the movable chassis and connected to the support beam, wherein the driven member is configured to be driven by the driving member by movement of the movable chassis in the first direction, thereby rotating the support beam to the first position or the second position.

3. The vehicle pulling device of claim 2, wherein
when the movable chassis is located in a first travel position, the driven member begins to be driven by the driving member, and when the movable chassis travels to a second travel position, the driven member is separated from the driving member.

4. The vehicle pulling device of claim 2, wherein
the driven member is a friction wheel, while the driving member is a friction belt.

5. The vehicle pulling device of claim 4, further comprising:
a shaft;
wherein the friction wheel is connected to the support beam through the shaft.

6. The vehicle pulling device of claim 5, further comprising:
a position limit member for limiting a rotation range of the friction wheel, wherein the position limit member limits the rotation range of the friction wheel within a range of about 90 degrees.

7. The vehicle pulling device of claim 4, further comprising:
a position limit member for limiting a rotation range of the friction wheel,
wherein the friction wheel has a recess extending in a circumferential direction and having a first end and a second end, and the position limit member is capable of contacting with the first end and the second end to limit the rotation range of the friction wheel.

8. The vehicle pulling device of claim 2, wherein
the driven member is disposed below the movable chassis.

9. The vehicle pulling device of claim 1, wherein
the support beam has depressed portions on upper surfaces of both ends, wherein when the support beam is in the first position, the wheels of the vehicle are engaged with the depressed portions on the upper surfaces of both ends of the support beam so that the vehicle is pulled to pass through the passage.

10. The vehicle pulling device of claim 9, wherein
each of both ends of the support beam has ramp portions on both sides, and the depressed portion is located between the ramp portions.

11. A system for passing a vehicle in two modes, comprising:
a passage through which a vehicle passes; and
a vehicle pulling device disposed in the passage, the vehicle pulling device comprising a movable chassis movable in a first direction in which the vehicle travels; and
a support beam disposed to the movable chassis and being rotatable between a first position and a second position, wherein:
in the first position, the support beam is located substantially in a second direction substantially perpendicular to the first direction, such that wheels of the vehicle are interacted with the support beam of the vehicle pulling device so that the vehicle is pulled to pass through the passage; and in the second position, the support beam is located substantially parallel to the first direction such that the wheels of the vehicle are not interacted with the support beam of the vehicle pulling device so that the vehicle travels by itself to pass through the passage.

12. The system of claim 11, further comprising:
a groove disposed in a ground surface in the passage, wherein the movable chassis travels in the groove.

13. The system of claim 12, wherein
when the support beam is in the second position, bottom surfaces of both ends of the support beam are higher than the ground surface.

14. The system of claim 12, wherein
the groove is located substantially at a middle portion of the passage in the second direction.

15. An inspection system for scanning a vehicle by radiation, comprising:
a passage through which a vehicle passes;
a radiation source disposed on one side of the passage;
a radiation receiving device disposed on the other side of the passage to receive the radiation passing through the vehicle under inspection; and
a vehicle pulling device comprising a support beam and configured for enabling the vehicle to pass through the passage in a first direction in a first mode and a second mode, wherein in the first mode, the support beam of the vehicle pulling device is located substantially in a second direction substantially perpendicular to the first direction, such that wheels of the vehicle are interacted with the support beam of the vehicle pulling device so that the vehicle is pulled to pass through the passage; and in the second mode, the support beam is located substantially parallel to the first direction such that the wheels of the vehicle are not interacted with the support beam of the vehicle pulling device so that the vehicle travels by itself to pass through the passage.

* * * * *